United States Patent [19]
Patel et al.

[11] Patent Number: 5,652,639
[45] Date of Patent: Jul. 29, 1997

[54] INDIRECT OPHTHALMOSCOPE PRODUCING AN ERECT STEREOSCOPIC IMAGE

[76] Inventors: Achyut S. Patel, 4314 Conifer Ct., Glen Arm, Md. 21057; Suresh R. Chandra, 4713 County Rd. M, Middleton, Wis. 53562

[21] Appl. No.: 608,489

[22] Filed: Feb. 28, 1996

[51] Int. Cl.$^6$ .................. A61B 3/10; A61B 3/00
[52] U.S. Cl. ........................... 351/205; 351/200
[58] Field of Search ................... 351/205, 206, 351/207, 208, 221, 200; 359/407, 833, 835, 857, 861, 399, 404

[56] References Cited

U.S. PATENT DOCUMENTS

| | | |
|---|---|---|
| 3,475,082 | 10/1969 | Strietzel . |
| 3,586,414 | 6/1971 | Schultz . |
| 3,600,067 | 8/1971 | Heine . |
| 3,625,601 | 12/1971 | Augusto et al. . |
| 3,685,887 | 8/1972 | Spurney . |
| 3,847,470 | 11/1974 | Dederer et al. . |
| 3,945,712 | 3/1976 | Crock et al. . |
| 3,963,329 | 6/1976 | Stumpf et al. . |
| 4,015,898 | 4/1977 | Schirmer . |
| 4,065,208 | 12/1977 | Currey . |
| 4,176,920 | 12/1979 | Ito . |
| 4,248,505 | 2/1981 | Muchel et al. . |
| 4,671,631 | 6/1987 | Sigelman . |
| 4,699,480 | 10/1987 | Pomerantzeff . |
| 4,710,000 | 12/1987 | Spitznas et al. . |
| 4,710,002 | 12/1987 | Pomerantzeff . |
| 4,786,161 | 11/1988 | Müller et al. . |
| 4,810,083 | 3/1989 | Okada et al. . |
| 4,838,678 | 6/1989 | Hubertus . |
| 4,963,014 | 10/1990 | Heine et al. . |
| 4,978,212 | 12/1990 | Hazard . |
| 5,223,863 | 6/1993 | Heine et al. . |
| 5,333,018 | 7/1994 | Heine et al. . |

OTHER PUBLICATIONS

M. Spitznas, et al., "A stereoscopic diagonal inverter (SDI) for wide-angle vitreous surgery", Graefe's Arch. Clin. Exp. Ophthalmol., vol. 225, pp. 9–12, 1987.

M. Spitznas, "A binocular indirect ophthalmomicroscope (BIOM) for non-contact wide-angle vitreous surgery", Graefe's Arch. Clin. Exp. Ophthalmol., vol. 225, pp. 13–15, 1987.

K.E. Schirmer, "The Upright Fundus Image in Indirect Ophthalmoscopy", Arch. Ophtal., vol. 77, pp. 67–70, Jan. 1967.

*Primary Examiner*—Hung X. Dang
*Attorney, Agent, or Firm*—Foley & Lardner

[57] ABSTRACT

An indirect ophthalmoscope is designed to provide a properly oriented stereoscopic image of the retina or vitreous of an eye from an inverted image produced by a condensing lens. The ophthalmoscope re-orients the inverted indirect image in the vertical direction using a primary image inverting assembly including two primary reflecting surfaces mounted at right angles for each one of right and left indirect images. The inverted indirect image is re-oriented in the horizontal direction using a secondary image flipping assembly including two secondary reflecting surfaces mounted in a trapezoidal relation for each of the left and right images. The secondary image flipping assembly also splits the images, re-directing the left and right indirect images to right and left eyepieces, respectively, of the ophthalmoscope to provide a true stereoscopic image. The reflecting surfaces employed in the ophthalmoscope are preferably implemented using highly reflective mirrors or as prisms employing total internal reflection. The ophthalmoscope of the present invention includes an illumination unit for providing illumination of the retina-vitreous under observation, and a head strap whereby the ophthalmoscope and illumination unit may be supported on the head of an observer.

35 Claims, 4 Drawing Sheets

INDIRECT OPHTHALMOSCOPE PRODUCING AN ERECT STEREOSCOPIC IMAGE

FIELD OF THE INVENTION

The present invention relates generally to devices for observation of the retina and vitreous humor in the eyes of humans and other creatures, and more particularly to optical devices known as ophthalmoscopes employing an indirect method of observation whereby an image created by a condensing lens is perceived.

BACKGROUND OF THE INVENTION

An ophthalmoscope is an instrument for examining the fundus oculi or concave interior of the eye, particularly the retina, optic disk, and visible blood vessels. Ophthalmoscopes are also used for examination of the vitreous body, the clear jelly that fills the eyeball posterior to the lens. Ophthalmoscopes may be monocular or binocular, the latter providing a stereoscopic view of the fundus, and generally are categorized as direct ophthalmoscopes or indirect ophthalmoscopes.

The direct ophthalmoscope is typically a hand-held instrument which illuminates and magnifies the fundus. Since the fundus is viewed directly, the image seen is erect rather than inverted. Typically, however, the practitioner must position his or her eye in close proximity to the instrument and patient. Moreover, the direct image has a narrow field of view and lacks depth because it is focused with only one of the examining practitioner's own eyes. For these reasons, the direct ophthalmoscope is generally unsuitable for surgical use.

In indirect ophthalmoscopes, a magnifying lens, known as a condensing lens, is interposed between the subject eye and the observer. Thereby, an image of the fundus is created at an image plane located between the patient and the viewer. This is known as indirect ophthalmoscopy, because the image which is viewed by the observer is the image created by the condensing lens. Typically, the condensing lens is used in conjunction with a binocular observation device which reduces the practitioner's interpupillary distance, allowing for stereoscopic viewing of the fundus image. This observation device also typically provides illumination of the fundus under observation.

The aerial image of the retina or vitreous produced by the condensing lens of the indirect ophthalmoscope is inverted and flipped spatially (i.e., left-to-right) with respect to the true original subject. The true retina-vitreous relationships cannot, therefore, be perceived directly. They can only be recreated after further processing, such as by drawing or photography. This creates a problem for the observer, and particularly the eye surgeon who must conduct precise operations in real space on the subject eye to achieve the goals of retinal-vitreous diagnosis and treatment. Since the surgeon's image is inverted in the vertical and flipped in the horizontal plane, his or her manipulations on the eye seem flipped and inverted. Thus, manipulations on the eye are made hazardous.

The condensing lens also reverses the relationship between left and right images of the original object. This becomes a problem when a true oriented stereoscopic image of the eye structure under observation is to be created.

Devices have been presented in the prior art which create a properly oriented fundus image using indirect ophthalmoscopy. These include the device described in U.S. Pat. No. 3,475,082 to Strietzel which describes a stereo ophthalmoscope which produces a correctly oriented stereo image using a separating prism to divide image rays into left and right images and reflecting surfaces or prisms to direct the images to eyepieces. A reversing lens system then forms a properly oriented image. U.S. Pat. No. 4,015,898 to Schirmer describes a wide angle stereo ophthalmoscope which produces an upright, unreversed stereo image using a single Uppendahl prism which inverts, reverses, and separates the rays passing therethrough from the condensing lens. U.S. Pat. No. 4,248,505 to Muchel, et al., describes a stereo ophthalmoscope using a prism and lens system for splitting and reversing the indirect image. U.S. Pat. Nos. 4,699,480 and 4,710,002 to Pomerantzeff describe magnifying stereo ophthalmoscopes using mirrors for splitting and transiently reversing the indirect image. U.S. Pat. No. 4,710,000 to Spitznas, et al. describes a stereo surgical microscope which uses reflecting prisms or mirrors for reversing an image. U.S. Pat. No. 4,786,161 to Müller, et al. describes a stereo ophthalmoscope device using two sets of four identical Porro prisms for image interchange and inversion. U.S. Pat. No. 4,838,678 to Hubertus describes a magnifying binocular ophthalmoscope using Schmidt or Pechan prisms to invert an image.

Use of many of these devices, however, is made difficult by their size and the requirement of a short working distance from the subject eye. Working distance is a particularly important consideration in operating room environments, where contamination of the sterile working field is a continuous concern, and where unnecessary restrictions on the surgeon's work space are to be avoided. In particular, prior art indirect ophthalmoscopes which present a properly oriented image often involve the use of a contact lens on the subject eye. These contact lenses are wide-field lenses, which, due to the large field angle, give reduced resolution of details of the fundus. Moreover, the contact lens can interfere with surgical activities. Devices adapted to operating microscopes have also been created which re-orient indirect images of the retina-vitreous. However, these devices are not portable.

Known ophthalmoscopes use a combination of lenses and complex prisms, in addition to mirrors, to reorient the indirect image of the eye structures of interest. However, the use of lenses in such systems introduce chromatic and spherical aberrations into the images. The use of complex prisms can further introduce image distortion. Finally, image brightness is lost with each optical manipulation.

There are several examples of ophthalmoscopes in the prior art which re-orient an inverted image. It is the object of this invention, however, to provide an optical system to reorient the indirect ophthalmoscopic image while maintaining stereopsis and image clarity without the aberrations attendant to prior art types of optical manipulation.

SUMMARY OF THE INVENTION

The present invention provides an improved indirect ophthalmoscope which creates a true stereoscopic erect image. Clarity and proper orientation of the patient eye image are achieved via the optical inversion of a condensing lens image by a series of reflecting surfaces which reorient sequentially in the vertical and in the horizontal planes while left and right images derived from the condensing lens are transmitted to the contralateral surgeon's eye, producing true stereopsis. The reflective surfaces reside in a head-mounted indirect ophthalmoscope in combination with an illumination housing linked to a head-strap worn by the surgeon. Standard non-contact condensing lenses are employed. The reflecting surfaces are preferably right angle prism surfaces employing total internal reflection principles or mirrors with high reflective efficiency.

In accordance with the present invention, a hand-held condensing lens is used to reproduce images of a fundus-vitreous region under observation in an image plane. This image of the object, for example, the retina, is inverted in the vertical and horizontal planes. Also, left and right images are re-oriented to the right and left, respectively. The ophthalmoscope of the present invention employs a primary image inverting assembly to flip the indirect image, properly re-orienting the image in the vertical plane. The primary image inverting assembly includes two sets of primary reflecting devices. Each set of primary reflecting devices includes two reflecting surfaces at right angles to each other. One set of primary reflecting devices is provided for flipping each of the left and right indirect images. The reflecting devices may preferably be formed of highly reflective mirrors with their reflective surfaces mounted at right angles to each other, or right angle prisms having two reflective surfaces and employing total internal reflection (TIR) principles.

The left and right flipped images are then each processed by a secondary image reversing assembly. The secondary image reversing assembly re-orients the indirect image in the horizontal plane, and splits the image, directing the left image to the right eye of the observer and the right image to the left eye of the observer. The secondary image reversing assembly includes two sets of secondary reflecting devices. Each set of secondary reflecting devices, one set each for the left and right images, includes two reflecting surfaces facing each other in a trapezoidal configuration. The reflecting surfaces in combination re-orient the indirect image in the horizontal direction and transmit the left and right indirect images to contralateral eyepieces (right and left, respectively) of the ophthalmoscope. The secondary reflecting devices may also be formed using highly reflective mirrors or prisms. The spacing between the reflecting surfaces of each set of secondary reflecting devices may preferably be adjustable, along with the spacing between the eyepieces, to match the interpupillary distance of the observer.

The physical positions of the primary and secondary reflecting devices are preferably staggered to provide an equal optical path length from the object under observation to the ophthalmoscope eyepieces for each of the right and left images. The primary and secondary reflecting devices can be arranged with respect to each other so that the ophthalmoscope first inverts the indirect image in the horizontal plane and then flips the image in the vertical plane, or first flips the indirect image in the vertical plane and then inverts the indirect image in the horizontal plane. The primary and secondary reflecting devices, which properly re-orient the inverted indirect image in the vertical and horizontal planes, may be retro-fitted into an existing ophthalmoscope system if desired.

The ophthalmoscope of the present invention includes two eyepieces, one for each eye of the observer. Each eyepiece is preferably coupled to the last reflecting surface in one of the secondary reflecting devices via a lens barrel. Each barrel is preferably set on a movable slide so that the interpupillary distance of the observer can be set appropriately by moving the eyepieces and last reflecting surfaces in combination. Similarly, the first reflecting surfaces of the secondary reflecting devices, which split the indirect image into left and right images, may preferably be movable on an axis perpendicular to the optical axis to allow for adjustment of the patient pupil size. This may be accomplished using a standard rack and pinion system.

The reflecting devices and eyepieces of the ophthalmoscope of the present invention are preferably provided in an observation unit enclosure. A standard head strap may be attached to the observation unit. The ophthalmoscope may thereby rest on an observer's head during use.

The ophthalmoscope of the present invention also preferably includes an illuminator, attached to the observation unit, for illumination of the eye under observation. Emitted light from the illuminator may be generated from a halogen bulb and directed into a subject's eye via an adjustable mirror located above the entrance site to the primary reflecting devices. A focusing lens is preferably used between the halogen bulb and the adjustable mirror.

Further objects, features and advantages of the invention will be apparent from the following detailed description when taken in conjunction with the accompanying drawings.

DETAILED DESCRIPTION OF THE INVENTION

Figure 1:
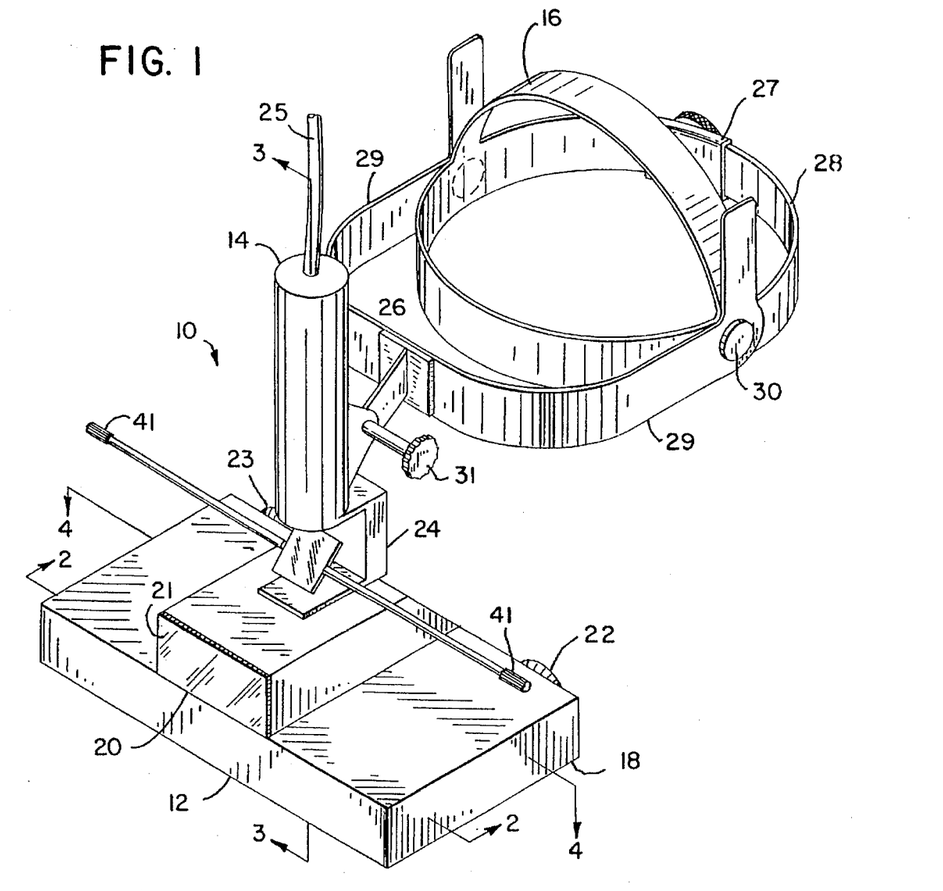
FIG. 1 is a perspective view of a stereoscopic erect image indirect ophthalmoscope in accordance with the present invention.

A stereoscopic erect image indirect ophthalmoscope in accordance with the present invention is described generally with reference to the perspective view of FIG. 1. The ophthalmoscope, shown generally at 10, includes as its major components an observation unit 12, an illuminator 14, and a head strap support 16.

The observation unit 12 may include a simple box-like structure 18 which encloses the optical components, to be described in more detail below, which properly re-orient the inverted image created by an ophthalmoscopic condensing lens. The observation unit enclosure 18 is preferably made of an opaque material which prevents undesirable external light from interfering with the examination of a patient's eye. The observation unit 12 includes an optical aperture 20, or window 20, through which reflected light from the eye under observation passes into the observation unit 12. The aperture 20 is preferably closed by a plain glass covering 21 to prevent the intrusion of dust into the observation unit 12. The glass covering 21 should be of high quality so as to prevent the distortion or attenuation of light passing through it. On the side of the observation unit 12 opposite the window 20 are two eyepieces 22 and 23 through which a true stereoscopic image of the interior of the patient's eye may be observed.

The illumination unit 14 is preferably mounted on the observation unit 12 such as by use of a bracket 24. As will be discussed in more detail below, the illumination unit 14 includes a light source which is connected to an electrical power source via a cable 25 which extends from the illumination unit 14. The other end of the cable 25 is connected to an electrical power source, such as a battery pack (not shown).

The head strap 16 is preferably attached to the observation unit 12 or the illumination unit 14 by an adjustable bracket 26. The head strap 16 may be of any standard design of common use. The head strap 16 is used to rest the observation unit 12 and illumination unit 14 on an observer's head during use of the ophthalmoscope. The head strap 16 preferably includes a standard type adjustment assembly 27 to permit adjustment of the size of the head strap band 28. Support arms 29 connect the bracket 26 to the band 28 of the head strap 16. The support arms 29 are preferably hinged 30 where they join with the head strap band 28. This allows the observation unit 12 to be flipped up, out of an observer's line of sight, when the ophthalmoscope 10 is not in use. Finer positioning of the observation unit 12 with respect to the eyes of an observer is preferably made possible by an adjustment knob 31 on the bracket 26. By adjustment of the knob 31, the observation unit 12 and illumination unit 14 may be rotated up or down with respect to the bracket 26 in order to better position the observation unit 12 with respect to the observer.

Figure 2:
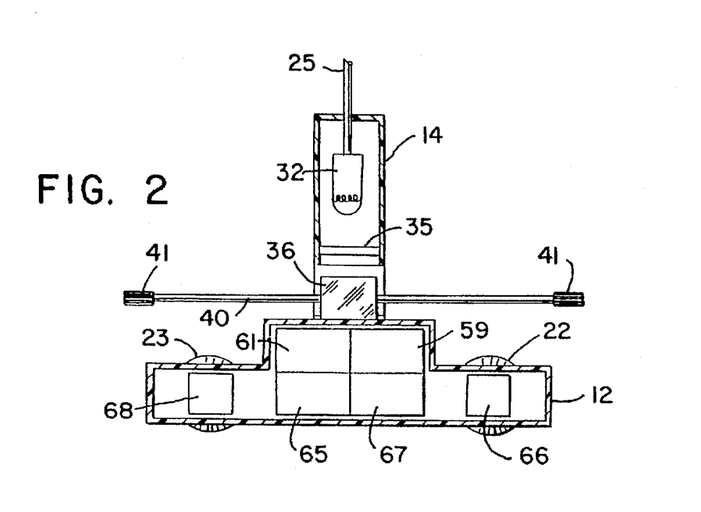
FIG. 2 is an illustrative front view, in cross-section of a stereoscopic erect image indirect ophthalmoscope in accordance with the present invention as taken along the line 2—2 of FIG. 1.
Figure 3:
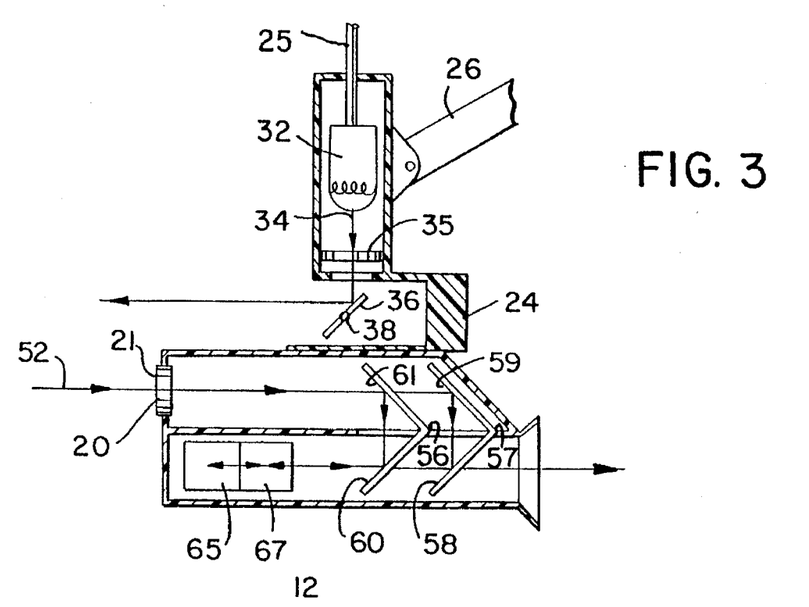
FIG. 3 is an illustrative side view, in cross-section, of a stereoscopic erect image indirect ophthalmoscope as taken along the line 3—3 of FIG. 1.

The operation of the illumination unit 14 to provide for the illumination of an eye under observation is described in more detail with reference to FIGS. 2 and 3. The illumination unit 14 includes an illumination source 32, such as a conventional linear coil filament halogen lamp, connected by the cable 25 to a power source (not shown). Cooling for the lamp 32 may be provided in any conventional manner, such as by providing vents (not shown) in the housing of the illumination unit 14. The lamp 32 is mounted in the illumination unit 14 so as to direct a beam of illumination light 34 through a focusing lens 35 towards an adjustable mirror 36. The focusing lens 35 may be fixed to focus the beam of illumination light 34 at a distance from the ophthalmoscope 10 at which an eye will typically be under observation, or may be made adjustable. The mirror 36 re-directs the beam of illumination light 34 toward the eye under observation. The mirror 36 is mounted so as to be rotatable around a pivot axis 38. By rotation of the mirror 36, the direction of the illumination beam 34 may be altered. As shown in FIG. 2, a rotatable rod 40 is connected to the mirror 36 along the pivot axis 38. The rod 40 is rotatably mounted on the observation unit 12. Knobs 41 are attached at ends of the rod 40, thereby permitting adjustment of the mirror angle. The rod 40 and mirror adjustment knobs 41 may be mounted with respect to the observation unit 12 in any manner commonly known in the art such that the mirror angle may be adjusted by turning the knobs 41, and the mirror angle will remain fixed otherwise. In other words, the mirror angle should not change unless one of the knobs 41 is turned.

Figure 4:
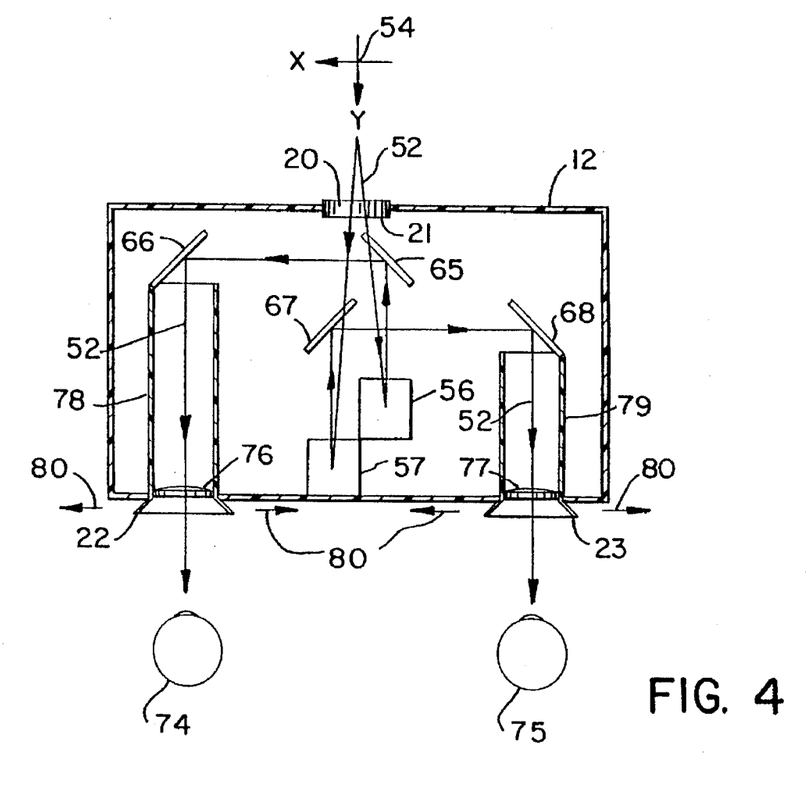
FIG. 4 is an illustrative plan view, in cross-section, of a stereoscopic erect image indirect ophthalmoscope as taken along the line 4—4 of FIG. 1.
Figure 5:
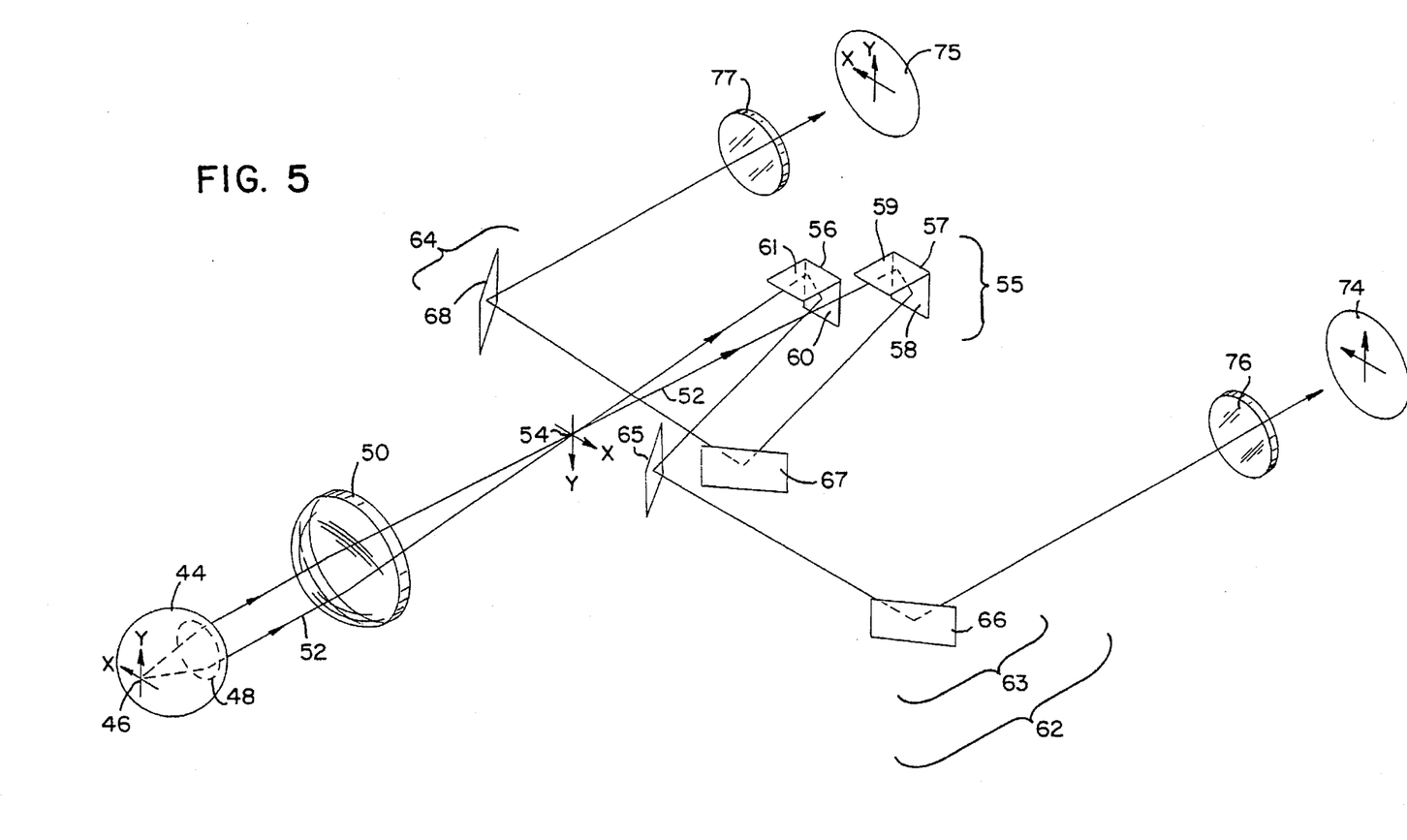
FIG. 5 is an illustrative schematic view, in perspective, of the optical components of a stereoscopic erect image indirect ophthalmoscope in accordance with the present invention.

The operation of the stereoscopic erect image indirect ophthalmoscope of the present invention for the proper stereoscopic re-orientation of an inverted indirect image is best illustrated with reference to FIGS. 2–5. Referring to FIG. 5, a patient's eye 44 is schematically shown. The eye 44 includes a fundus area 46, containing the retina, at the back of the eye 44. Opposite the fundus 46 is the lens 48 of the eye 44. The X-Y axis shown drawn in the fundus area 46 represents the true orientation of a portion of the fundus 46 under observation, such as the retina. In other words, the orientation of the X-Y axes as shown represents the image of the retina as viewed directly.

For indirect observation of the retina 46, a condensing lens 50 is placed between the subject eye 44 and the ophthalmoscope observation unit 12. The condensing lens 50 will typically be hand-held. Rays of light 52 are reflected from the retina 46 and are emitted from the eye 44. These rays pass through the eye lens 48, emerging from the eye 44 as a bundle of light rays 52. The rays 52 are formed into an inverted image 54 by the condensing lens 50. The inverted image lies in a plane between the condensing lens 50 and the observation unit 12 and the orientation of the image is indicated by the orientation of the X-Y axes at 54. The condensing lens 50 also generally acts to magnify the image of the retina 46.

The light rays 52, in fact, include right and left images of the fundus 46 which may be overlayed to provide stereopsis. The condensing lens 50, however, interchanges the positions of the right and left images. For example, two bundles of light rays emitted from the eye 44, each emanating from the fundus 46 at points near each other, but separated to the left and right of each other, will be interchanged by the condensing lens 50 so that the rays from the left image bundle will appear on the right of the rays from the right image bundle in the indirect image 54.

The light rays 52 continue from the (inverted indirect) image 54 through the window 20 into the observation unit 12. In the unit 12, the indirect image 54 is first effectively re-oriented in the vertical plane by a primary image inverting assembly 55. The primary image inverting assembly 55 includes two sets of primary reflecting devices 56 and 57. Each set of primary reflecting devices includes two reflecting surfaces 58, 59 and 60, 61 at right angles to each other. One of the primary reflecting devices 57 flips the left image, and the other primary reflecting device 56 flips the right image. Note that the primary reflecting devices also reverse the direction of the image rays 52.

The primary reflecting surfaces 58–61 may preferably be implemented using highly reflective mirrors. For example, 16.8×22.7×1.0 mm mirrors (31417) made by Edmond Scientific, of Barrington, N.J. may be used. The mirrors may be cemented or otherwise connected together at a right angle, with their reflective surfaces facing each other, in a conventional manner. Alternatively, the primary reflecting devices 56 and 57 may be implemented with right angle prisms employing total internal reflection (TIR) principles. Each right angle prism has a hypotenuse surface and two TIR reflecting surfaces which correspond to reflecting surfaces 58–61. The hypotenuse surface is the entrance and exit surface for light rays passing through the prism. The hypotenuse surface is coated with an anti-reflective coating, and is oriented to be normal to incident light rays.

After being vertically re-oriented, the incoming light is further processed by a secondary image reversing assembly 62. The secondary image reversing assembly 62 both re-orients the indirect image horizontally, and splits the image, transmitting the left and right indirect images to contralateral eyepieces, i.e., to the right and left respectively, of the ophthalmoscope 10. The secondary image reversing assembly includes two sets of secondary reflecting devices 63 and 64. There is one set of secondary reflecting devices for each of the left and right images. Each set consists of a first reflecting surface 65 or 67 and a last reflecting surface 66 or 68. The secondary reflecting surfaces may be implemented using the highly reflective mirrors described above. The mirrors are mounted within the observation unit 12 in a conventional manner so that the first reflecting surfaces 65 and 67 face the last reflecting surfaces 66 and 68, respectively, in a trapezoidal configuration. Alternatively, the reflecting surfaces 65–68 may be implemented using right angle TIR prisms. The hypotenuses of the prisms would form reflecting surfaces, corresponding to reflecting surfaces 65–68, which face each other in a trapezoidal configuration. The other side surfaces of the prisms would provide light entrance and exit surfaces. The side surfaces of the prisms are thus preferably coated with an anti-reflective coating.

As is shown, the first secondary reflecting surfaces 65 and 67 split the indirect image, re-directing the right and left images to the contralateral, left and right, eyepieces 22 and 23, respectively. The combination of all of the secondary reflecting surfaces 65–68 re-orients the indirect images in the horizontal direction. Note that the secondary reflecting surfaces 65–68 also reverse the direction of the image rays 52.

Figure 6:
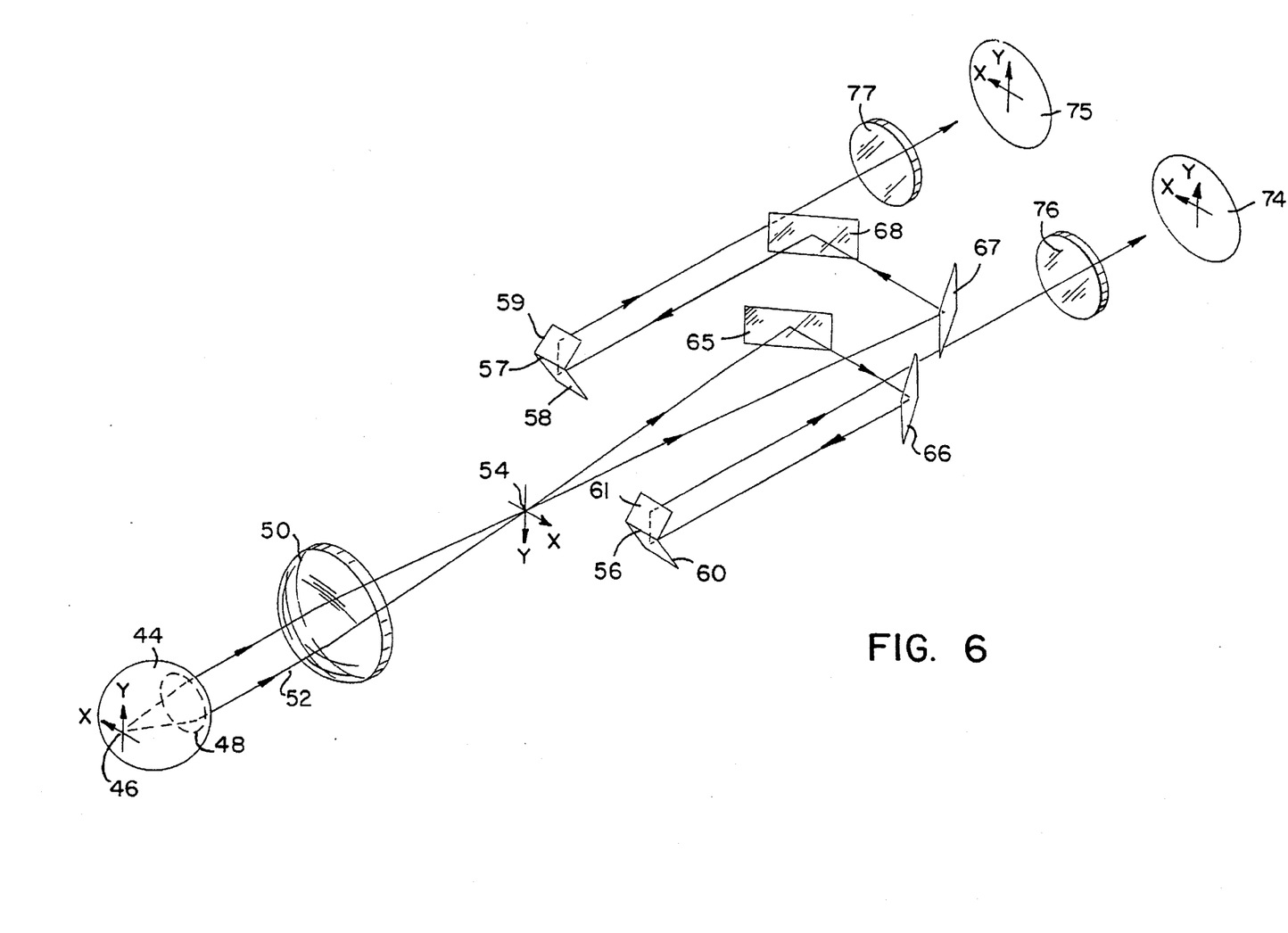
FIG. 6 is an illustrative schematic view, in perspective, of an alternative arrangement of the optical components of a stereoscopic erect image indirect ophthalmoscope in accordance with the present invention.

The primary reflecting surfaces 58–61 and secondary reflecting surfaces 65–68 combine to re-orient inverted indirect images 54, directing a properly oriented stereo image to the eyes 74 and 75 of an observer. The positions of the primary and secondary reflecting surfaces are physically staggered to provide an equal optical path length from the object being viewed 46 to the eyepieces 22 and 23. For each of the left and right images, the relative positions of the primary reflecting surfaces 58–61 and secondary reflecting surfaces 65–68 may be interchanged, as shown in FIG. 6. The components of FIG. 6 have the same function as the components of FIG. 5, and are, therefore, labeled with the same reference numerals. However, the arrangement of the components with respect to the incoming image rays 52 has been altered. Thus, the reflecting surfaces 58–61 and 65–68 are arranged so that incoming rays 52, representing the inverted indirect image 54, first encounter the secondary reflecting surfaces 65–68 which re-orient the indirect image 54 in the horizontal direction, and split the image directing the true left and right images toward the left and right contralateral eyepieces 22 and 23. The horizontally re-oriented images are then operated on by the primary reflecting surfaces 58–61 to re-orient the images in the vertical direction before the image rays 52 reach the eyepieces 22 and 23. Thus, the reflecting surfaces 58–61 and 65–68 may be arranged in accordance with the present invention to first invert horizontally and then flip vertically the indirect images rather than first flip vertically and then invert horizontally the images, as is shown in FIG. 5.

The eyepieces 22 and 23 may be of standard design. Each eyepiece 22 and 23 preferably includes a +2.00 diopter lens 76 and 77 to provide accommodation for the observer. Each eyepiece 22 and 23 and lens 76 and 77 is preferably coupled to the last of the secondary reflecting surfaces 66 and 68 via a barrel 78 and 79, as shown in FIG. 4. The barrels 78 and 79 may be cylindrical or other structures which connect the reflecting surfaces 66 and 68 with the eyepieces 22 and 23 such that the reflecting surfaces 66 and 68 and eyepieces 22 and 23 remain rigidly aligned along the path of the light rays 52. The barrels 78 and 79 may be mounted in the observation unit 12 in a conventional manner so that the barrels 78 and 79 may be moved to the left or right as indicated by the arrows 80. Any desired mechanism, such as a conventional rack and pinion, may be employed to move the barrels in the direction perpendicular to the light rays 52 and to lock them in a desired position. Preferably, the movement of each barrel 78 and 79 is coordinated so that, when moved, each will move an identical distance inward or outward from the center of the observation unit 12. In this way, the interpupillary distance, the distance between the eyes 74 and 75 of the observer, may be adjusted while maintaining a constant optical path length for each (left and right) image. It should be noted that, if the alternate embodiment described above with respect to FIG. 6, where, the primary, vertically flipping, reflecting surfaces follow the secondary, horizontally inverting, reflecting surfaces, is used, a more complex barrel structure including both the primary reflecting surfaces 58–61 and the last secondary reflecting surfaces 66 and 68 must be used.

The first secondary reflecting surfaces 65 and 67 may also be mounted on a structure, not shown, such as a rack and pinion mechanism, that allows movement of these surfaces along the optical axis perpendicular to the movement of the last secondary reflecting surfaces 66 and 68). This allows these image splitting reflecting surfaces to be adjusted to the pupil size of the patient.

It is apparent from the above description and the schematic diagram of FIG. 5 that an inverted indirect image 54 produced by the condensing lens 50 is vertically and horizontally re-oriented, with left and right images split and passed to the proper eyepieces, using the stereoscopic inverting optical system of the present invention, including the primary reflecting surfaces 58–61 and secondary reflecting surfaces 65–68. Thus, the direct image of the object 46 (e.g., an area of the retina) is recreated, as magnified by the condensing lens 50 and eyepiece lenses 76 and 77, at the eyes 74 and 75 of the observer. Since only reflecting devices are used to invert and direct the image, the chromatic and spherical aberrations which may be introduced by the use of refracting devices, i.e., lenses, and the image distortions which can be introduced by complex prisms, are avoided.

The reflecting surface arrangement of the present invention may be retro-fitted into an existing ophthalmoscope to provide the desired vertical and horizontal re-orientation. For instance, the primary and secondary reflecting surfaces 58–61 and 65–68 may be included as part of an ophthalmic microscope or other device having an objective lens as an integral part of the device.

It is understood that the invention is not confined to the particular embodiments set forth herein as illustrative, but embraces all such forms thereof as come within the scope of the following claims.

What is claimed is:

1. An indirect ophthalmoscope for producing an erect true stereoscopic image of a patient fundus from inverted and reversed left and right images produced by a condensing lens comprising:

(a) a primary image inverting assembly to invert the images produced by the condensing lens in a vertical direction, the primary image inverting assembly including two sets of primary reflecting devices, each set of primary reflecting devices including two reflecting surfaces oriented such that each set of primary reflecting devices inverts a one of the right or left images in a vertical direction; and (b) a secondary image reversing assembly to reverse the images produced by the condensing lens in a horizontal direction and to split and interchange the left and right images produced by the condensing lens to direct them along right and left optical pathways toward eyepieces of the ophthalmoscope, the secondary image reversing assembly including two sets of secondary reflecting devices, each set of secondary reflecting devices including a first reflecting surface and a last reflecting surface, the first and last reflecting surfaces oriented facing each other such that each set of secondary reflecting devices inverts a one of the right or left images in a horizontal direction and such that the sets of secondary reflecting devices interchange the right and left images to thereby direct the right and left images produced by the condensing lens to left and right optical pathways, respectively.

2. The indirect ophthalmoscope of claim 1 wherein the primary and secondary reflecting surfaces are highly reflective mirrors.

3. The indirect ophthalmoscope of claim 1 wherein the primary reflecting surfaces of each set of primary reflecting devices are mounted at right angles to each other and wherein the first and last reflecting surfaces of each set of secondary reflecting devices are mounted in a trapezoidal relation with respect to each other.

4. The indirect ophthalmoscope of claim 1 wherein the primary image inverting assembly and secondary image reversing assembly are arranged so that the inverted images are first inverted in the vertical direction by the primary reflecting devices and then flipped in the horizontal direction by the secondary reflecting devices.

5. The indirect ophthalmoscope of claim 1 wherein the primary image inverting assembly and secondary image reversing assembly are arranged so that the inverted images are first flipped in the horizontal direction by the secondary reflecting devices and then inverted in the vertical direction by the primary reflecting devices.

6. The indirect ophthalmoscope of claim 1 wherein a distance between the first and last reflecting surfaces of the secondary reflecting devices is adjustable.

7. The indirect ophthalmoscope of claim 1 comprising additionally left and right eyepieces wherein a one of the last reflecting surfaces directs the right image produced by the condensing lens to the left eyepiece and the other of the last reflecting surfaces directs the left image produced by the condensing lens to the right eyepiece.

8. The indirect ophthalmoscope of claim 7 wherein each eyepiece includes a lens.

9. The indirect ophthalmoscope of claim 8 wherein the eyepiece lens is a +2.00 diopter lens.

10. The indirect ophthalmoscope of claim 7 wherein each eyepiece is connected to a one of the last reflecting surfaces such that the eyepiece and last reflecting surface may be moved together the same distance to adjust the distance between the eyepieces and between the first and last reflecting surfaces so that an interpupillary distance of a user can be matched.

11. The indirect ophthalmoscope of claim 7 wherein the primary image inverting assembly, secondary image reversing assembly, and eyepieces are combined into an ophthalmoscope observation unit including an observation unit enclosure, and comprising additionally a head strap attached to the observation unit for supporting the observation unit on the head of an observer.

12. The indirect ophthalmoscope of claim 11 comprising additionally an illumination unit attached to the observation unit for providing illumination light for the illumination of an eye under observation.

13. The indirect ophthalmoscope of claim 12 comprising additionally means for adjusting a direction of the illumination light.

14. The indirect ophthalmoscope of claim 13 wherein the means for adjusting the direction of the illumination light includes a rotatable mirror mounted on the observation unit.

15. The indirect ophthalmoscope of claim 1 wherein positions of the primary and secondary reflecting devices are staggered such that left and right optical pathways are offset to obtain equal path lengths.

16. An indirect ophthalmoscope for producing an erect true stereoscopic image of a patient fundus from inverted and reversed left and right images produced by a condensing lens comprising:

(a) an observation unit including right and left eyepieces, a primary image inverting assembly to invert the images produced by the condensing lens in a vertical direction, the primary image inverting assembly including two sets of primary reflecting devices, each set of primary reflecting devices including two reflecting surfaces oriented such that each set of primary reflecting devices inverts a one of the right or left images in a vertical direction, and a secondary image reversing assembly to reverse the images produced by the condensing lens in a horizontal direction and to split and interchange the left and right images produced by the condensing lens to direct them along right and left optical pathways toward the eyepieces of the ophthalmoscope, the secondary image reversing assembly including two sets of secondary reflecting devices, each set of secondary reflecting devices including a first reflecting surface and a last reflecting surface, the first and last reflecting surfaces oriented facing each other such that each set of secondary reflecting devices inverts a one of the right or left images in a horizontal direction and such that the sets of secondary reflecting devices interchange the right and left images produced by the condensing lens such that a one of the last reflecting surfaces directs the right image produced by the condensing lens to the left eyepiece and the other of the last reflecting surfaces directs the left image produced by the condensing lens to the right eyepiece;

(b) an illumination unit attached to the observation unit for providing illumination light for the illumination of an eye under observation; and (c) a head strap attached to the observation unit for supporting the observation unit and illumination unit on the head of an observer.

17. The indirect ophthalmoscope of claim 16 wherein the primary and secondary reflecting surfaces are highly reflective mirrors.

18. The indirect ophthalmoscope of claim 16 wherein the primary reflecting surfaces of each set of primary reflecting devices are mounted at right angles to each other and wherein the first and last reflecting surfaces of each set of secondary reflecting devices are mounted in a trapezoidal relation with respect to each other.

19. The indirect ophthalmoscope of claim 16 wherein each eyepiece includes a lens.

20. The indirect ophthalmoscope of claim 19 wherein the eyepiece lens is a +2.00 diopter lens.

21. The indirect ophthalmoscope of claim 16 wherein each eyepiece is connected to a one of the last reflecting surfaces such that the eyepiece and last reflecting surface may be moved together the same distance to adjust the distance between the eyepieces and between the first and last reflecting surfaces so that an interpupillary distance of a surgeon can be matched.

22. The indirect ophthalmoscope of claim 16 comprising additionally means for adjusting a direction of the illumination light.

23. The indirect ophthalmoscope of claim 22 wherein the means for adjusting the direction of the illumination light includes a rotatable mirror mounted on the observation unit.

24. The indirect ophthalmoscope of claim 16 wherein positions of the primary and secondary reflecting devices are staggered such that left and right optical pathways are offset to obtain equal path lengths.

25. An indirect ophthalmoscope for producing an erect true stereoscopic image of a patient fundus at eyepieces of the ophthalmoscope from inverted and reversed left and right images produced by a condensing lens comprising:

(a) two sets of horizontally inverting reflecting devices, each set of horizontally inverting reflecting devices including a first reflecting surface and a second reflecting surface, the first and second reflecting surfaces oriented facing each other such that each set of horizontally inverting reflecting devices flips a one of the right or left images in a horizontal direction and such that the sets of horizontally inverting reflecting devices interchange the right and left images produced by the condensing lens to thereby direct the right and left images produced by the condensing lens to left and right optical pathways respectively; and (b) two sets of vertically inverting reflecting devices, each set of vertically inverting reflecting devices including two reflecting surfaces oriented such that each set of vertically inverting reflecting devices inverts a one of the right or left images in a vertical direction and such that the sets of vertically inverting devices direct the erect image toward the eyepieces.

26. An indirect ophthalmoscope for producing an erect true stereoscopic image of a patient fundus from inverted and reversed left and right images produced by a condensing lens, comprising:

(a) a primary image inverting assembly to invert the images produced by the condensing lens in a vertical direction, the primary image inverting assembly including two sets of primary reflecting devices, each set of primary reflecting devices including two reflecting surfaces mounted at right angles to each other such that each set of primary reflecting devices inverts a one of the right or left images in a vertical direction;

(b) a secondary image reversing assembly to flip the images produced by the condensing lens in a horizontal direction and to split and interchange the left and right images produced by the condensing lens to direct them along right and left optical pathways towards eyepieces of the ophthalmoscope, the secondary image reversing assembly including two sets of secondary reflecting devices, each set of secondary reflecting devices including a first reflecting surface and a last reflecting surface, the first and last reflecting surfaces mounted facing each other in a trapezoidal relation wherein the distance between the first and last reflecting surfaces is adjustable and such that each set of secondary reflecting devices flips a one of the right or left images in a horizontal direction and such that the sets of secondary reflecting devices interchange the right and left images to thereby direct the right and left images produced by the condensing lens to left and right optical pathways, respectively, and wherein positions of the primary and secondary reflecting devices are staggered such that left and right optical pathways are offset to obtain equal path lengths; and (c) left and right eyepieces connected to the last reflecting surfaces of the secondary sets of reflecting devices by a moveable means for moving the eyepieces and the last reflecting surfaces together to adjust the distance between the eyepieces and the first and last reflecting surfaces so that the interpupillary distance of a surgeon can be matched.

27. An indirect ophthalmoscope for producing an erect true stereoscopic image of a patient fundus from inverted and reversed left and right images produced by a condensing lens, comprising:

(a) a primary image inverting assembly to invert the images produced by the condensing lens in a vertical direction, the primary image inverting assembly including two sets of primary reflecting devices, each set of primary reflecting devices including two reflecting surfaces oriented such that each set of primary reflecting devices inverts a one of the right or left images in a vertical direction;

(b) a secondary image reversing assembly to reverse the images produced by the condensing lens in a horizontal direction, the secondary image reversing assembly including two sets of secondary reflecting devices, each set of secondary reflecting devices including a first reflecting surface and a last reflecting surface, the first and last reflecting surfaces oriented facing each other such that each set of secondary reflecting devices inverts a one of the right or left images in a horizontal direction; and (c) means for interchanging the left and right images to thereby direct the left and right images produced by the condensing lens along right and left optical pathways towards right and left eyepieces of the ophthalmoscope, respectively.

28. The indirect ophthalmoscope of claim 27 wherein the means for interchanging the left and right images includes the first and last reflecting surfaces of the secondary image reversing assembly oriented with respect to the primary reflecting devices such that the sets of secondary reflecting devices also interchange the left and right images to thereby direct the left and right images produced by the condensing lens to right and left optical pathways, respectively.

29. The indirect ophthalmoscope of claim 27 wherein the primary and secondary reflecting devices are highly reflective mirrors.

30. The indirect ophthalmoscope of claim 27 wherein the primary reflecting surfaces of each set of primary reflecting devices are mounted at right angles to each other and wherein the first and last reflecting surfaces of each set of secondary reflecting devices are mounted in a trapezoidal relation with respect to each other.

31. The indirect ophthalmoscope of claim 27 wherein the primary image inverting assembly and secondary image reversing assembly are arranged so that the inverted images are first inverted in the vertical direction by the primary reflecting devices and then flipped in the horizontal direction by the secondary reflecting devices.

32. The indirect ophthalmoscope of claim 27 comprising additionally left and right eyepieces wherein a one of the last reflecting surfaces directs the right image produced by the condensing lens to the left eyepiece and the other of the last reflecting surfaces directs the left image produced by the condensing lens to the right eyepiece.

33. The indirect ophthalmoscope of claim 32 wherein the primary image inverting assembly, secondary image reversing assembly, and eyepieces are combined into an ophthalmoscope observation unit including an observation unit enclosure, and comprising additionally a head strap attached to the observation unit for supporting the observation unit on the head of an observer.

34. The indirect ophthalmoscope of claim 33 comprising additionally an illumination unit attached to the observation unit for providing illumination light for the illumination of an eye under observation.

35. The indirect ophthalmoscope of claim 27 wherein positions of the primary and secondary reflecting devices are staggered such that the left and right optical pathways are offset to obtain equal path lengths.

* * * * *